United States Patent [19]

Wheatley et al.

[11] Patent Number: 4,933,185

[45] Date of Patent: Jun. 12, 1990

[54] SYSTEM FOR CONTROLLED RELEASE OF BIOLOGICALLY ACTIVE COMPOUNDS

[75] Inventors: Margaret A. Wheatley, Norristown, Pa.; Robert S. Langer, Somerville; Herman N. Eisen, Waban, both of Mass.

[73] Assignee: Massachusetts Institute of Technology, Cambridge, Mass.

[21] Appl. No.: 223,887

[22] Filed: Jul. 11, 1988

Related U.S. Application Data

[63] Continuation of Ser. No. 910,884, Sep. 24, 1986, abandoned.

[51] Int. Cl.$^5$ .................. A61K 9/62; A61K 39/00; B01J 13/02
[52] U.S. Cl. .................. 424/461; 424/88; 424/14.3; 424/469; 428/402.2; 428/402.21; 514/885; 514/963
[58] Field of Search .......... 428/402.2, 402.21, 88, 428/94.3, 461, 469; 514/963

[56] References Cited

U.S. PATENT DOCUMENTS

| | | | |
|---|---|---|---|
| 3,493,652 | 2/1970 | Hartman | 424/94.63 X |
| 3,522,346 | 9/1970 | Chang | 424/491 |
| 3,964,973 | 6/1976 | Hradil, et al. | 424/94.63 X |
| 4,251,387 | 2/1981 | Lim et al. | 264/4.3 |
| 4,255,411 | 3/1981 | Lim et al. | 424/1.1 |
| 4,257,884 | 3/1981 | Lim | 210/656 |
| 4,311,690 | 2/1982 | Buehler et al. | 424/1.1 |
| 4,322,311 | 3/1982 | Lim et al. | 264/4.7 |
| 4,324,683 | 4/1982 | Lim et al. | 264/4.3 |
| 4,352,883 | 10/1982 | Lim | 435/178 |
| 4,386,895 | 6/1983 | Sodickson | 425/5 |
| 4,389,419 | 6/1983 | Lim et al. | 426/72 |
| 4,391,909 | 7/1983 | Lim | 435/178 |
| 4,407,957 | 10/1983 | Lim | 435/178 |
| 4,409,331 | 10/1983 | Lim | 435/178 |
| 4,495,288 | 1/1985 | Jarvis, Jr. et al. | 435/241 |
| 4,532,123 | 7/1985 | Gardner | 428/402.2 X |
| 4,585,651 | 4/1986 | Beck et al. | 424/88 |

OTHER PUBLICATIONS

Boyd, et al., *Carbohydrate Reasearch* 57, 163–171 (1977).
Sutherland, et al., *J. Applied Biochem.* 3, 48–57 (1981).
von Reisen, *Applied and Environmental Microbiology* 39 (1), 92–96, (Jan. 1980).
Davidson, et al., *Biochem. J.* 159, 707–713 (1976).

*Primary Examiner*—Richard D. Lovering
*Attorney, Agent, or Firm*—Kilpatrick & Cody

[57] ABSTRACT

A controlled release system for delivery of a biologically-active substance. In one embodiment, there is a delayed release of a biologically-active substance. In a second embodiment, the delayed release is preceded by an initial release of biologically active substance. In other variations of the system, there are mulitple discrete releases over time or a continuous slow release combined with discrete releases. The delayed exposure is achieved through the design and construction of the system, specifically, formation of ionically-coated microcapsules around the biologically-active substance in conjunction with a microcapsule core-degrading enzyme. Release of active substance takes place in a burst at such a time as the core degrading enzyme has reduced the core to a molecular weight too low to support enough interaction with the cationic skin to maintain its integrity as a skin. In one example, microcapsules are formed of an ionically cross-linked polysaccharide, calcium alginate, which is further ionically coated with a poly-cationic skin of poly-L-lysine. The capsule coating serves a dual purpose: to control diffusion of the biologically-active substance and the core-degrading enzyme and as a substrate for the mechanism by which the biologically-active substance is released after a time delay.

25 Claims, No Drawings

SYSTEM FOR CONTROLLED RELEASE OF BIOLOGICALLY ACTIVE COMPOUNDS

This is a continuation of U.S. Ser. No. 910,884 entitled "A System for Controlled Release of Biologically Active Compounds" filed Sept. 24, 1986 by Margaret A. Wheatley, Robert S. Langer, and Herman N. Eisen now abandoned.

BACKGROUND OF THE INVENTION

The present invention is generally in the area of controlled release of biologically-active compounds and in particular is a system for controlled release of biologically-active substances within specifically formulated microcapsules in conjunction with a microcapsule core-degrading enzyme.

Encapsulation of biological material as a method for delivery of a biologically-active substance, both in vivo and in vitro, is well known. U.S. Pat. No. 4,352,883 to Lim entitled "Encapsulation of Biological Material" discloses encapsulation or a core material such as living cells or proteins within a membrane that is permeable to small molecules but impermeable to larger molecules. Encapsulation is carried out by suspending the core material in an aqueous medium containing a water-soluble gum that can be reversibly gelled, forming the suspension into droplets, contacting the droplets with a solution of multivalent cations to gel the droplets as discrete, shape-retaining, water insoluble temporary capsules and ionically cross-linking a surface layer of the temporary capsules to produce a semipermeable membrane around the capsules.

The system disclosed in U.S. Pat. No. 4,352,883 relates to a process for encapsulating tissue or individual cells so that they remain viable and in a protective state within a membrane which is permeable to nutrients, ions, oxygen and other materials needed to both maintain the tissue and support its normal metabolic functions, but impermeable to bacteria, lymphocytes, and large proteins of the type responsible for immunochemical reactions resulting in rejection. In the preferred embodiment of this system, the microcapsule retains its integrity following implantation.

The technology for forming a microcapsule around a labile biologically-active substance, such as many of the glycoproteins, is well known. A two-step interfacial polymerization process for encapsulating operative chemically-active substances within semipermeable membranes is disclosed in U.S. Pat. No. 4,324,683 to Lim et al entitled "Encapsulation of Labile Biological Material". The purpose of this method is to form microcapsules with a well-controlled porosity. The microcapsule serves to protect the active substances from attack by microorganisms. Accordingly, the purpose of this disclosed method is the same as in U.S. Pat. No. 4,352,883, i.e., to preserve and protect the encapsulated material and, in particular, to avoid any immunological response against the encapsulated biologically-active material.

Methods have been developed to reversibly encapsulate biologically-active substances. For example, as disclosed by Lim in U.S. Pat. No. 4,407,957, a biologically-active material may be encapsulated and subsequently released by selective disruption of the membranes in the microcapsules. As disclosed, the encapsulation technique involves the formation of a semipermeable membrane around a droplet through the formation of multiple ionic bonds between a polyionic polymer in the droplet and a cross-linking polyionic polymer which possesses multiple ionic groups of opposite charge. The membrane can be selectively disrupted by exposing it first to a solution of competing cross-linking multivalent ions followed by a solution of a competing polyionic polymer of the same charge as the polymer in the original droplet. Alternatively, a mixed solution of the two competing solutions may be used together. Unfortunately, such a process of reversal is limited to in vitro use, for example, for the encapsulation and subsequent release of cell cultures without damage to the cells.

Another method for encapsulating biologically-active substances for subsequent release which is useful both in vivo and in vitro is described in U.S. patent applications Ser. No. 07/161,198, now U.S. Pat. No. 4,900,556, which is a continuation of U.S. Ser. No. 727,802 entitled "System for Delayed and Pulsed Release of Biologically-Active Substances" (now abandoned) and Ser. No. 07/092,554 allowed, which is a continuation of U.S. Ser. No. 727,803 entitled "System and Apparatus for Delayed and Pulsed Release of Biologically-Active Substances"(now abandoned), both filed Apr. 26, 1985 by Margaret A. Wheatley, Robert S. Langer and Herman N. Eisen. A system for controlled release of entrapped biologically-active substances, either at a constant rate over a period of time or in discrete pulses, is disclosed. The biologically-active substances are entrapped within liposomes, which are protected from the biological environment by encapsulation within semipermeable microcapsules or a permeable polymeric matrix. Release of the entrapped substance into the surrounding environment is governed by the permeability of both the liposome and the surrounding matrix to the substance. Permeability of the liposome is engineered by modifying the composition and method for making the liposomes to produce liposomes which are sensitive to a specific stimuli, such as temperature, pH or light; by including a phospholipase within some or all of the liposomes or the surrounding matrix which degrade the liposomes; by destabilizing the liposome to break down over a period of time; or by any combination of these methods. While this method is useful both in vitro and in vivo for a controlled rate of release, the system and apparatus require expertise in the processing and handling of both liposomes and microcapsules, as well as the delicate interrelationship between the two, to achieve the desired result.

It is therefore an object of the present invention to provide a method for controlled release which is useful both in vitro and in vivo.

It is a further object of the present invention to provide a method for controlled release which is simple, reliable, and versatile.

It is a further object of the invention to provide a system for controlled release which can be used for single, delayed, or multiple release of the substances over time.

It is another object of the invention to provide a system for controlled release of biologically-active substances including labile proteins as well as more stable organic and inorganic molecules.

SUMMARY OF THE INVENTION

A controlled release system for delivery of a biologically-active substance consisting of a biologically-active substance and an enzyme encapsulated within a microcapsule having a core formed of a polymer which is specifically degraded by the enzyme and a rate controlling skin. The integrity of the skin is lost when the core is degraded, causing a sudden release of biologically-active substance from the capsule. In one embodiment, the system provides an initial exposure of the biologically-active substance, followed by one or more delayed exposures following a specific period of time. In other embodiments where the skin is impermeable to the biologically active substance, a single delayed release of the biologically-active substance occurs following degradation of the microcapsule. In still other embodiments, the skin is partially permeable to the biologically-active substance, allowing for continuous release in conjunction with one or more pulsed releases of biologically-active substance. The system is versatile and can be modified to produce a combination of continuous and pulsed release of the same or different biologically-active substances.

In the preferred embodiment of the controlled release system, the microcapsule consists of a core made up of a polymer around which there is an ionically-bound skin. The integrity of the skin depends on the structure of the core. An enzyme is encapsulated with the biologically-active substance to be released during manufacture of the core of the microcapsule. The enzyme is selected to degrade the core to a point at which the core can no longer maintain the integrity of the skin, so that the capsule falls apart. In one embodiment, the capsule system consists of ionically cross-linked polysaccharide, calcium alginate, which is ionically-coated with a polycationic skin of poly-L-lysine. The enzyme used to degrade the calcium-alginate coated with poly-L-lysine microcapsules is an alginase from the bacteria *Beneckea pelagia* or *Pseudomonas putida*. Enzymes exist that degrade most naturally-occurring polymers. For example, the capsule core may be formed of chitin for degradation with chitinase. Other natural or synthetic polymers may also be used and degraded with the appropriate enzyme, usually a hydrolase.

There are a number of practical applications for the controlled release system. For example, antigen and the appropriate enzyme may be encapsulated within a microcapsule for injection with free antigen into an animal to provide both an initial and a subsequent exposure to the antigen to promote maximum immunological response. This avoids the problems inherent in repeat immunizations with livestock or in remote areas where doctors must spend days of travel to reach isolated areas. In another example, the microcapsules can be used as a means for disbursing inorganic compounds at the appropriate time. For example, where a system has a slow rate of absorption, the microcapsules may be used to provide an extended time of release so that more material is absorbed efficiently. A third example is in the area of hormone therapy, where discrete bursts of hormone at specific times (daily or longer cycles) are required.

DETAILED DESCRIPTION OF THE INVENTION

The present invention is a system for controlled release consisting of a substance to be released and an enzyme which are encapsulated within a microcapsule having both a core polymer and an ionically-bound skin, wherein the enzyme specifically degrades the microcapsule core polymer.

A variety of substances can be encapsulated with the enzyme. Examples of biologically-active substances are proteins (such as enzymes, hormones, and globulins), polyamino acids, nucleic acids, drugs, vitamins, small virus particles, and other small molecules, including inorganic materials such as pesticides and nutrients. Other substances such as dyes may also be encapsulated with the enzyme. Each system must be examined individually for compatibility between the enzyme, the biologically-active substance, and the material forming the microcapsule. The individual components should be selected to provide the minimum of interaction between the enzyme and the biologically-active substance, and the biologically-active substance should not interact with the microcapsule core. The ionically-bound skin of the microcapsule should also be formed so that it is relatively impermeable to both the enzyme and the biologically-active substance. However, it may be designed to provide for a slow rate of release of the biologically-active substance over time, followed by a burst of biologically-active substance after degradation of the microcapsule core by the encapsulated enzyme. The enzyme may be modified, for example with a coating of polyethylene glycol, so that it is not recognized by the immune system upon release from the capsule. The biologically-active substance and the enzyme may also be modified so they are retained within the microcapsule pending complete degradation of the microcapsule core. For example, the enzyme and/or the biologically-active substance may be cross-linked to increase their molecular weight or they may be bound to a solid matrix such as Sepharose ™ (Pharmacia Fine Chemicals, N.J.).

In the method of the present invention, the biologically-active substance and enzyme are encapsulated within a permeable polymeric matrix consisting of any non-toxic polymer or mixture of polymers which can be polymerized using a method which does not harm the biologically-active substance and enzyme, which results in a matrix of the desired thickness, rigidity, permeability, and stability, and for which there is a specific enzyme which will degrade the monomer linkages after a period of time.

The preferred method for making capsules is taught by U.S. Pat. No. 4,352,883 to Lim. Using this method, 500 micron diameter (sized by gel filtration) capsules with a permeability of approximately 6,000 to 40,000 m.w. are formed with a core of alginate cross-linked with calcium ions selectively coated with a polycationic skin using polymers such as poly-L-lysine and poly-vinylamine. The microcapsule size can be reduced (for example below 200 microns for injection) by increasing the spraying speed at the droplet forming stage. The process is as follows: the biologically-active substance and enzyme are encapsulated in a physiologically-compatible medium containing a water soluble substance that can be made insoluble (gelled). The medium is then formed into droplets around the biologically-active substance and enzyme and gelled by changing temperature, pH or ionic strength. The gelled droplets are then treated to produce membranes of a controlled permeability about the gelled droplets. The preferred material for forming the temporary capsules is a polysaccharide gum, either natural or synthetic, of the type which can be gelled to form a shape-retaining mass by exposure to a different pH or multivalent cations, such as $Ca^{++}$, and ionically cross-linked by polymers containing reactive groups such as amine or imine groups which can react with acidic polysaccharide constituents. Gelatin or agar may be used in place of the polysaccharide gums.

There are a number of enzymes produced by bacteria and other organisms which specifically degrade polysaccharides including amylose, cellulose and pectin, and mucopolysaccharidases, including hyaluronic acid, chitin, mucopolysaccharides formed from N-acetyl-D-muramic acid and 2-acetylamino-2-deoxy-D-glucose, and neuraminic acid. For example, when the microcapsule core is formed of algin, a copolymer of D-mannuronic acid and L-guluronic acid, in which blocks of one type of monosaccharide residues are separated by segments in which the two residues alternate, the preferred enzyme for encapsulation would be alginase. There are two groups of alginases, one which severs D-mannuronic acid linkages and one which severs L-guluronic acid linkages. Sources of alginase in the first group include *Beneckea pelagia* and *Klebsiella aerogenes*. Examples of sources of the second group of alginases include *Pseudomonas putida, Pseudomonas maltophilia, Azobacter vinelandii*, and tissues such as the hepatopancreas of the abalone. Methods for isolating alginases are taught by I. W. Sutherland et al in *J. App. Biochem.* 3, 48–57 (1981); V. Lyle von Riesen in *App. Environ. Microbiol.*, 39(1), 92–96 (1980); Ian W. Davidson et al in *Biochem. J.*, 159, 707–713 (1976); and J. Boyd et al in *Carbohydrate Research*, 57, 163–171 (1977).

The protein can be reacted with polyethylene glycol according to the method of Davis et al. in *Lancet* 2, 281–283 (1981) for in vivo applications where it is desirable to modify the core degrading enzyme in such a way that it is not recognized by the immune system.

The preferred method of formation of the droplets to be gelled is to use a syringe pump to force the sodium alginate suspension through a capillary tube or 22-gauge needle around which flows a coaxial stream of air. Droplets ejected from the tip of the needle immediately contact a 1.5% $CaCl_2$ solution and gel as spherical bodies.

The preferred method of formation of a permanent semipermeable membrane about the temporary capsules of cross-linked polysaccharide is to cross-link surface layers of the gelled alginate using a dilute solution of polyamino acids such as poly-L-lysine and poly-vinylamine. Generally, the lower the molecular weight of the polymer, the greater the penetration into the surface of the temporary capsule and the less permeable the resulting membrane. Ionic cross-links are produced as a consequence of salt formation between the cationic side groups of the cross-linking polymer and the acid groups of the polysaccharide gum. Within limits, permeability can be controlled by setting the molecular weight of the cross-linking polymer, its concentration, and the duration of the reaction.

It is possible to improve mass transfer within the capsule after formation of the permanent membrane by re-establishing the conditions under which the material forming the temporary capsule is liquid, for example, by removing the multivalent cations by ion exchange in a phospate-buffered saline containing citrate. This may hasten the degradation of the remaining core which interacts with the skin sine the enzyme will have greater access to the wall of the capsule.

Unlike previous methods utilizing microcapsules, the present method requires that the encapsulated enzyme act on the core polymer. When the integrity of the core polymer is sufficiently damaged, the outer skin of the microcapsule also loses its integrity and the encapsulated biologically-active substance is released.

In the preferred embodiment for use in delivering a substance in vivo, algin is used to form the microcapsule core. Algin is used in foods as a thickening and stabilizing agent, as described by W. H. McNeeley and D. F. Pettitt in *Industrial Gums: Polysaccharides and Their Derivatives*, 2nd Ed., R. L. Wistler and J. N. BeMiller, ed., p. 49–82 (Academic Press, Inc. N.Y. 1973). There is no similar requirement when the system is used in vitro with the exception that the material must not be toxic to the degrading enzyme.

A number of variations of the disclosed method are possible. In one embodiment, the system is used to provide a release of a biologically-active substance after a specific time delay. In another embodiment, the skin of the microcapsule is made permeable to small amounts of the biologically-active material, but not the degrading enzyme, so that a small amount is initially released over time, followed by a larger burst of biologically-active substance. In a third embodiment, the encapsulated enzyme and biologically-active substance is injected in vivo with a quantity of unencapsulated or free biologically-active substance. This embodiment is particularly useful for providing a two-stage vaccination of both animals or people. In a fourth embodiment, varying amounts of enzyme are encapsulated with the biologically-active substance within the microcapsules, alone or in conjunction with free biologicallyactive substance, to provide a series of multiple or continuous releases of biologically-active substances. Microcapsules containing different amounts of enzyme or enzyme with modified activity (where the total amount of enzyme is measured as units of enzymatic activity) may also be combined with different biological substances to provide for continuous and/or pulsed release of a variety of substances over an extended period of time.

The present invention may be embodied in other specific forms without departing from the spirit and scope thereof. These and other modifications of the invention will occur to those skilled in the art, keeping in mind the key feature of the invention is to provide a system for controlled release, in discrete pulses or in discrete pulses in combination with a continuous slow release over a specific period of time, of an encapsulated biologically-active substance. Such other embodiments and modifications are intended to fall within the scope of the appended claims.

I claim:

1. A system for controlled release of a biologically-active substance comprising:
    (a) microcapsules having an inner polysaccharide polymer core and an outer ionically interacting skin;
    (b) a biologically-active substance; and
    (c) an enzyme, said enzyme specifically degrading said core polysaccharide and not the ionically interacting skin;
    wherein said biologically-active substance and said enzyme are encapsulated in said microcapsules, said enzyme degrading said core polysaccharide until the outer skin loses its integrity, the microcapsules completely break down and said biologically-active substance is released.

2. The system of claim 1 further comprising non-encapsulated biologically-active substance.

3. The system of claim 1 wherein said enzyme is modified to be non-immunogenic.

4. The system of claim 1 wherein the molecular weight of said enzyme is altered.

5. The system of claim 1 wherein the polysaccharide is selected from the group consisting of alginate, chitin, pectin, gums, and combinations thereof and the enzyme is selected from the group consisting of polysaccharidases, mucopolysaccharidases, lyases, hydrolases, alginase, chitinase, amylase, cellulase, pectinase, hyaluronidase, lysozyme, neuraminidase, and combinations thereof.

6. The system of claim 1 wherein the permeability of said microcapsules is increased to allow continuous passage at a controlled rate of biologically-active substance out of said microcapsules.

7. The system of claim 1 wherein the units of enzymatic activity within said microcapsule are calibrated to degrade said core polysaccharide over a specified time and said microcapsules contain different total units of enzymatic activity.

8. The system of claim 1 comprising microcapsules of different size, said capsules catastrophically breaking down at different times.

9. The system of claim 8 comprising microcapsules with increased permeability to allow continuous passage of biologically-active substance out of said microcapsule.

10. The system of claim 1 comprising more than one biologically-active substance.

11. A method for controlled release of a biologically-active substance comprising:
    encapsulating the biologically-active substance and an enzyme within microcapsules, wherein said microcapsules are formed of an inner polysaccharide core and an outer ionically interacting skin, and said enzyme specifically degrades said polysaccharide core,
    locating said microcapsules at the site where controlled release is to occur, and
    reacting said encapsulated enzyme with said polysaccharide core to alter the integrity of said ionically interacting skin to completely break down the microcapsules and effect release of the biologically active substance from the microcapsules.

12. The method of claim 11 further comprising locating non-encapsulated biologically-active substance at the site for controlled release of said encapsulated biologically-active substance.

13. The method of claim 11 further comprising selecting the biologically-active substance from the group consisting of proteins, nucleic acids, viruses, and inorganic compounds.

14. The method of claim 11 further comprising selecting an enzyme which does not provoke an immune response.

15. The method of claim 11 further comprising selecting an enzyme modified to increase its molecular weight.

16. The method of claim 15 wherein the molecular weight of said enzyme is increased by cross linking of the enzyme itself or to other large molecular weight carriers.

17. The method of claim 11 further comprising selecting the polysaccharide from the group consisting of alginate, chitin, pectin, gums, and combinations thereof.

18. The method of claim 11 further comprising selecting the enzyme from the group consisting of polysaccharidases, mucopolysaccharidases, lyases, hydrolases, alginase, chitinase, amylase, cellulase, pectinase, hyaluronidase, lysozyme, neuraminidase, and combinations thereof.

19. The method of claim 11 wherein the biologically-active substance is encapsulated by dissolving a water-soluble polysaccharide gum in an aqueous solution containing the biologically-active substance and polysaccharide degrading enzyme to be encapsulated,
    forming droplets of the dissolved gum,
    cross-linking the polysaccharide gum, and
    forming a semipermeable membrane about the surface of the cross-linked droplets.

20. The method of claim 19 wherein the semipermeable membrane is formed by contacting the polysaccharide gum with a solution selected from the group consisting of water-soluble polyamines, diamines, polyols, diols, glutaraldehyde, and multifunctional sulfonyl halides.

21. The method of claim 19 wherein the semipermeable membrane is formed by contacting droplets formed of a water-soluble gum containing acid groups with a solution of multivalent cations.

22. A method for immunizing an animal comprising:
    encapsulating an antigen and an enzyme within microcapsules, wherein said microcapsules are formed of an inner core polysaccharide and an outer ionically interacting skin and said enzyme specifically degrades said core polysaccharide of the microcapsules to effect complete break down of the microcapsules and release of said encapsulated antigen, and injecting said microcapsules into the animal to be immunized.

23. The method of claim 22 comprising selecting an enzyme modified to be non-immunogenic.

24. The method of claim 22 further comprising selecting an enzyme that has been modified to increase its molecular weight.

25. The method of claim 22 further comprising injecting unencapsulated antigen with said microcapsule into said animal to be immunized.

* * * * *